United States Patent
Melsheimer (10) Patent No.: US 11,020,252 B2
(45) Date of Patent: Jun. 1, 2021

(54) LONGITUDINALLY FOLDED STENT AND METHOD OF USING SAME

(71) Applicant: Cook Medical Technologies LLC, Bloomington, IN (US)

(72) Inventor: Jeffry Scott Melsheimer, Springville, IN (US)

(73) Assignee: Cook Medical Technologies LLC, Bloomington, IN (US)

(*) Notice: Subject to any disclaimer, the term of this patent is extended or adjusted under 35 U.S.C. 154(b) by 182 days.

(21) Appl. No.: 16/238,892

(22) Filed: Jan. 3, 2019

(65) Prior Publication Data
US 2019/0209350 A1    Jul. 11, 2019

Related U.S. Application Data

(60) Provisional application No. 62/615,583, filed on Jan. 10, 2018.

(51) Int. Cl.
| | |
|---|---|
| *A61F 2/06* | (2013.01) |
| *A61F 2/844* | (2013.01) |
| *A61B 17/11* | (2006.01) |
| *A61F 2/95* | (2013.01) |
| *A61F 2/915* | (2013.01) |

(52) U.S. Cl.
CPC .............. *A61F 2/844* (2013.01); *A61B 17/11* (2013.01); *A61B 2017/1107* (2013.01); *A61B 2017/1132* (2013.01); *A61F 2/064* (2013.01); *A61F 2002/91541* (2013.01); *A61F 2002/91575* (2013.01); *A61F 2002/9511* (2013.01)

(58) Field of Classification Search
CPC .... A61F 2/844; A61F 2/95; A61F 2/07; A61F 2/966; A61F 2/958; A61F 2/91; A61F 2002/91541; A61F 2002/9511; A61F 2002/9534

See application file for complete search history.

(56) References Cited

U.S. PATENT DOCUMENTS

| | | | |
|---|---|---|---|
| 4,214,586 A | 7/1980 | Mericle | |
| 4,523,592 A | 6/1985 | Daniel | |
| 4,710,181 A | 12/1987 | Fuqua | |
| 4,766,898 A | 8/1988 | Hardy et al. | |
| 8,663,310 B2 * | 3/2014 | Greenberg | A61F 2/07 623/1.13 |
| 8,728,148 B2 | 5/2014 | Roeder et al. | |
| 2002/0045930 A1 | 4/2002 | Burg et al. | |
| 2002/0087176 A1 | 7/2002 | Greenhalgh | |

(Continued)

*Primary Examiner* — Vi X Nguyen
(74) *Attorney, Agent, or Firm* — Liell & McNeil (57) ABSTRACT

A stent assembly includes a framework having a tubular rest shape that defines a longitudinal axis, has an external surface that defines an expanded perimeter, and an internal surface that defines a passageway. The framework has a folded shape with a cross section perpendicular to the longitudinal axis that fits in a closed shape having a perimeter that is smaller than the expanded perimeter. The stent assembly has a constrained configuration characterized by the framework being held in the folded shape by a trigger wire supporting sheer stress by being in contact with interlaced loops of the framework. The stent assembly has an unconstrained configuration characterized by the framework being in the tubular rest shape with the trigger wire out of contact with the framework.

13 Claims, 12 Drawing Sheets (56) References Cited

U.S. PATENT DOCUMENTS

2006/0004393 A1    1/2006   Amarant
2010/0010610 A1    1/2010   Grevious
2015/0094744 A1    4/2015   Aghayev et al.

\* cited by examiner

LONGITUDINALLY FOLDED STENT AND METHOD OF USING SAME

TECHNICAL FIELD

The present disclosure relates generally to stents, and more particularly to a stent constrained in a folded shape by a trigger wire(s).

BACKGROUND

Both self expanding and balloon expanded stents have been well known for many years. In both cases, the stent is placed in a small diameter configuration for delivery to a treatment site, and then expanded to a larger diameter for implantation at the treatment site. Most of these stents include a framework constructed from bent wire, or are cut from a cannula to include numerous interconnected struts. The diameter of the stent is reduced for delivery often by reducing vertex angles between adjacent struts. While these stent construction and constraining strategies have seen considerable success, they have inherent limitations, and there is always room for improvement.

In one specific example, when doing reconstructive or transplant surgery, there are often tiny blood vessels (e.g., 1-5 mm. diameter) that need to be connected to keep tissues viable. Typically, these vessels are hand sutured in an often difficult and time consuming manner, or some device such as a Flow Coupler by Synovis is used. But these devices often create large, rigid couplings at an interface between the two vessels and in the middle of the surgical repair. Thus, making micro-vascular end to end anastomosis connections can be problematic and time consuming.

The present disclosure is directed toward one or more of the problems set forth above.

SUMMARY

In one aspect, a stent assembly includes a framework having a tubular rest shape that defines a longitudinal axis, has an external surface that defines an expanded perimeter, and an internal surface that defines a passageway. The stent assembly also includes a trigger wire. The framework has a folded shape with a cross section perpendicular to the longitudinal axis that fits within a closed shape having a perimeter that is smaller than the expanded perimeter. The stent assembly has a constrained configuration characterized by the framework being held in the folded shape by the trigger wire being in contact with at least one of the internal surface and the external surface to apply a shear force perpendicular to the longitudinal axis responsive to a bias of the framework to resiliently unfold. The stent assembly has an unconstrained configuration characterized by the framework being in the tubular rest shape with the trigger wire out of contact with the framework.

In another aspect, a method of joining two vessels end-to-end includes a step of sliding one end of a stent assembly in a constrained configuration into an open end of a first vessel. An opposite end of the stent assembly is slid in the constrained configuration into an open end of a second vessel. The stent assembly is changed from the constrained configuration to an unconstrained configuration responsive to moving at least one trigger wire from contact with a framework to a position out of contact with the framework. The framework is unfolded from a folded shape in the constrained configuration that fits within a closed shape oriented perpendicular to the longitudinal axis of the framework to a tubular rest shape with an expanded perimeter defined by an external surface of the framework that is larger than a perimeter of the closed shape.

DETAILED DESCRIPTION

Referring initially to FIGS. 1-8, a stent 29 according to the present disclosure includes a framework 31 having a tubular rest shape 32 that defines a longitudinal axis 37. The phrase "tubular rest shape" means a shape assumed by the framework absent any external forces. The framework has an external surface 33 that defines an expanded perimeter 34, and an internal surface 35 that defines a passageway 36. Although a stent 29 according to the present disclosure could be constructed from bent wire, stents 29 according to the present disclosure may more easily be cut from a solid wall tube which is made from a suitable alloy, such as a super-elastic and/or shape memory material, such as a nickel titanium alloy. In other words, while the present disclosure contemplates stents made from bent wire, stents according to the present disclosure may more preferably be cannula cut stents having a cut out pattern that facilitates overlapping and folding as described infra. Although not necessary, the tube may desirably have an aspect ratio between its major diameter and wall thickness on the order of 50:1. The tube may be etched, laser cut, machined or ground to cut features into the tube wall to create the framework shown, for instance in FIGS. 1 and 2. The framework pattern is chosen to produce a set of features that can be laced together over a trigger wire to keep the stent 29 constrained in a cross sectional shape that is a fraction of its original tubular rest shape diameter. Depending upon the desired application, the tube can be cut to include additional features that may be used, for instance to anchor the deployed stent at a fixed position within a vessel, or features that allow for the stent to have additional flexibility or have the ability to change in length and/or diameter away from its tubular rest shape.

Figure 1:
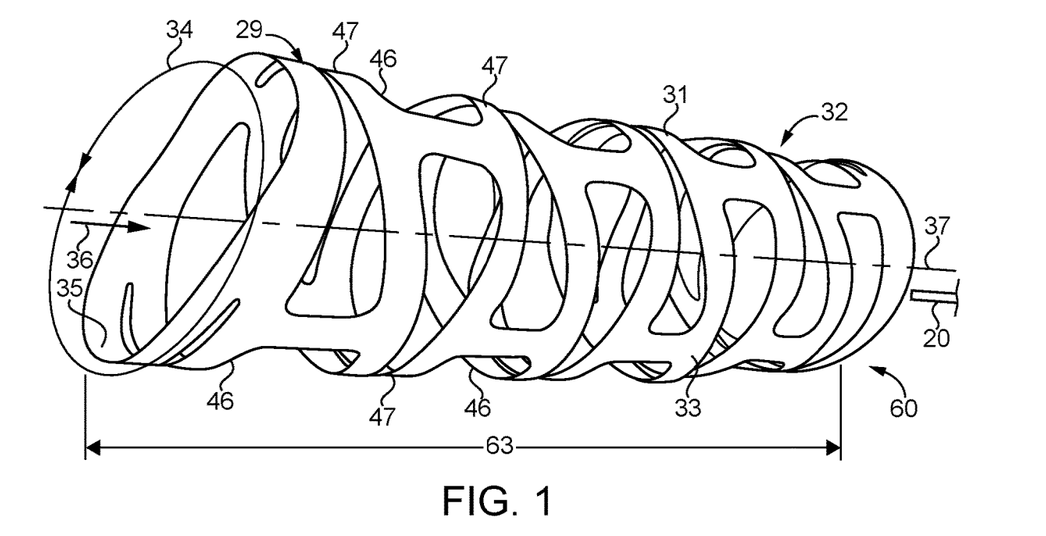
FIG. 1 is a perspective diagrammatic view of a stent according to the present disclosure in a tubular rest shape.
Figure 2:
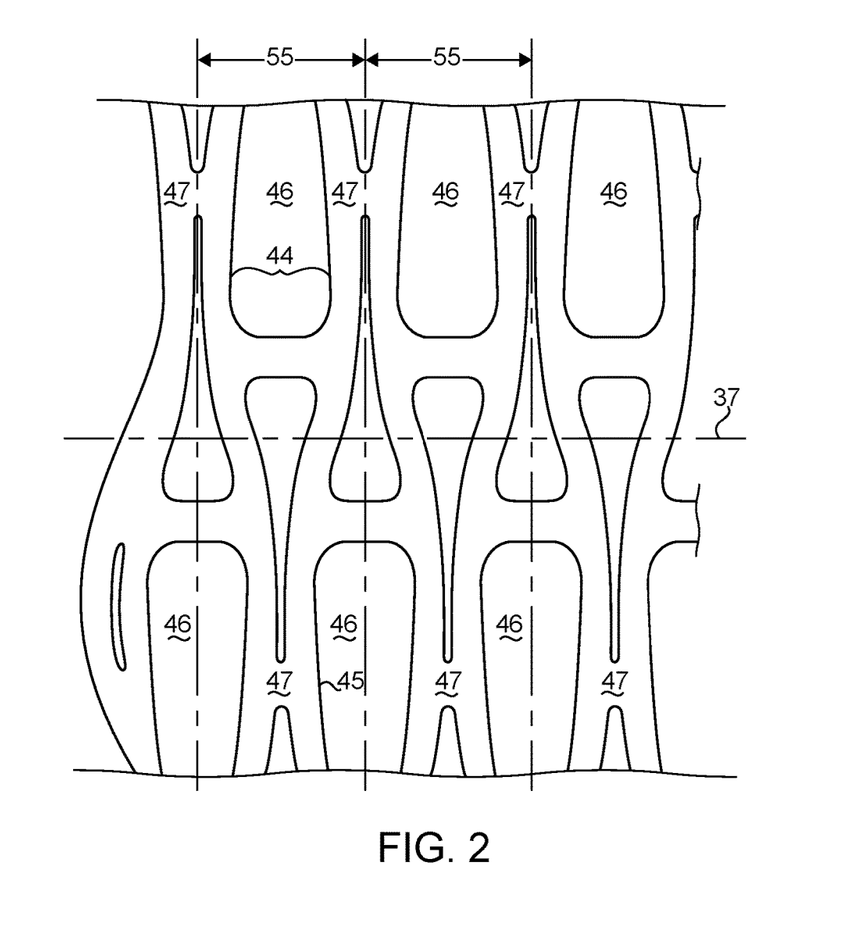
FIG. 2 is a flat layout of a cannula cut pattern for the stent of FIG. 1.
Figure 3:
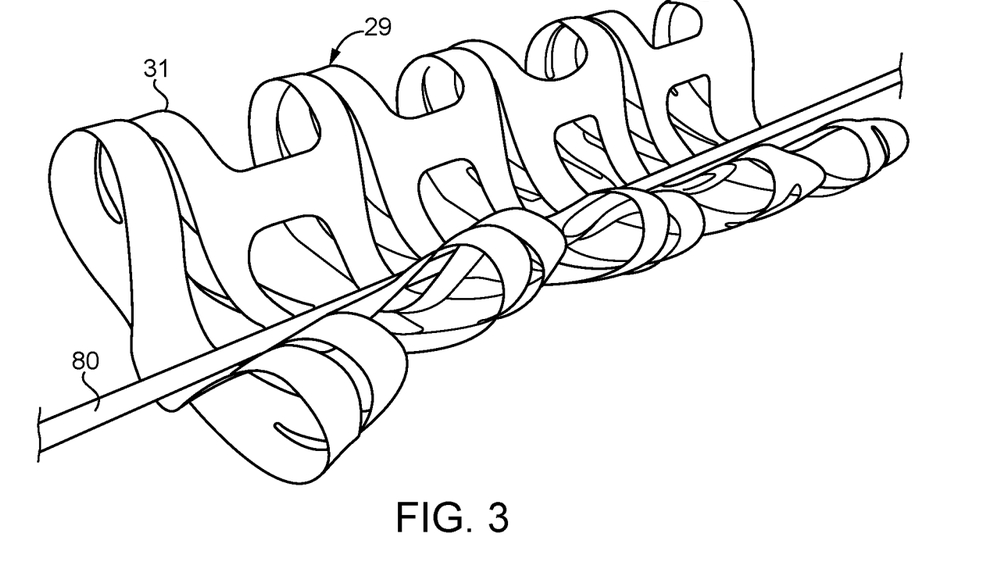
FIG. 3 is a perspective diagrammatic view of the stent of FIG. 1 during a folding procedure according to the present disclosure.
Figure 4:
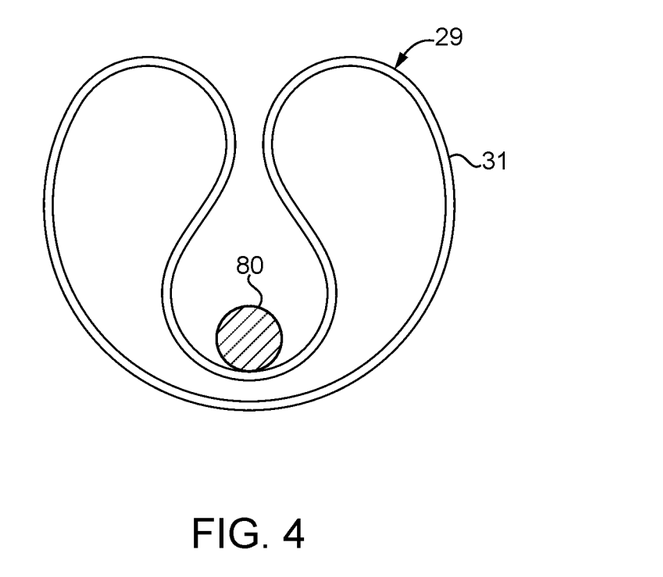
FIG. 4 is a schematic end view of the stent of FIG. 1 in the partially folded configuration of FIG. 3.

FIGS. 1 and 2 show an example framework pattern according to the present disclosure. FIGS. 3-7 are of interest for showing one strategy for folding stent 29 into a folded shape 40 with a cross section 41 perpendicular to the longitudinal axis 37 that fits within a closed shape 42, such as a circle, having a perimeter 43 that is smaller than the expanded perimeter 34 of the tubular rest shape 32. The term "perimeter" means the length of a perimeter, and is thus measurable. FIG. 3 shows a first step in a folding process for this specific framework 31 pattern. In this example, a first folding rod 80 is pressed against external surface 33 to cause the framework 31 to collapse toward the longitudinal axis 37 and fold in on itself so that the internal surface 35 on opposite sides of framework 31 may come in contact with each other. While keeping the folding rod 80 in place, the opposite sides on either side of folding rod 80 are folded toward a plane that contains folding rod 80 so that loops 47 formed on one side are received in windows 46 defined by the tubular framework on an opposite side of folding rod 80. Returning briefly to FIG. 2, the framework pattern may include a plurality of contiguous ring segments 55 that have identical patterns. Each ring segment 55 includes at least one window 46 and at least one loop 47 sized to be received in the respective window 46. Returning to FIG. 5, a trigger wire 20 may be inserted through each of the loops 47 and be in contact with the internal surface 35 to hold stent assembly 30, which includes stent 29 and the trigger wire 20, in a constrained configuration 61. In this embodiment, the trigger wire 20 is in contact with internal surface 35 at a plurality of discrete locations associated with each individual loop 47 over a distance 62 that is less than a length 63 of the framework along the longitudinal axis 37. Those with ordinary skill in the art will appreciate that the loops 47 apply a shear force to the trigger wire 20 perpendicular to the longitudinal axis 37 responsive to a bias of the framework 31 to resiliently unfold.

Figure 6:
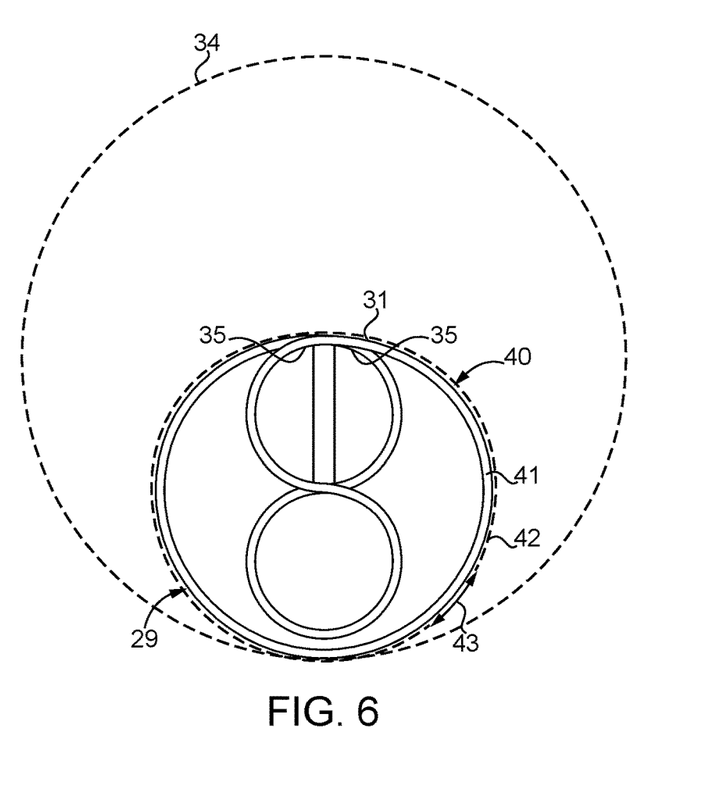
FIG. 6 is a schematic end view of the folded and constrained stent of FIG. 5.
Figure 7:
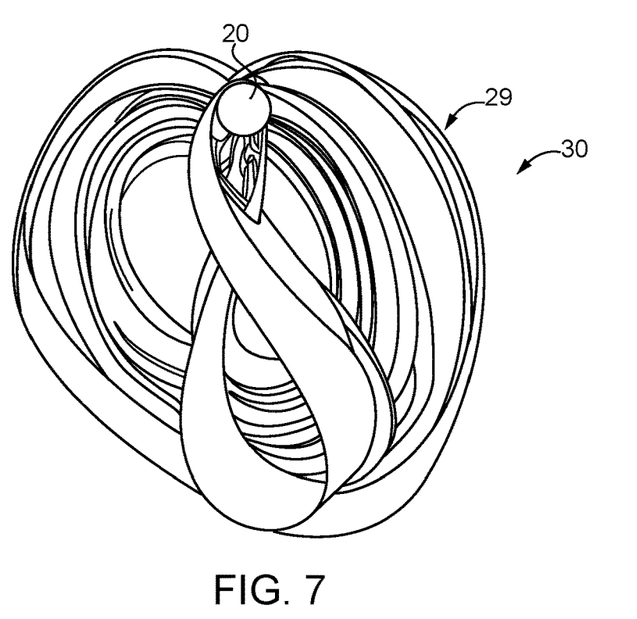
FIG. 7 is an end perspective diagrammatic view of the folded constrained stent of FIGS. 5 and 6.
Figure 8:
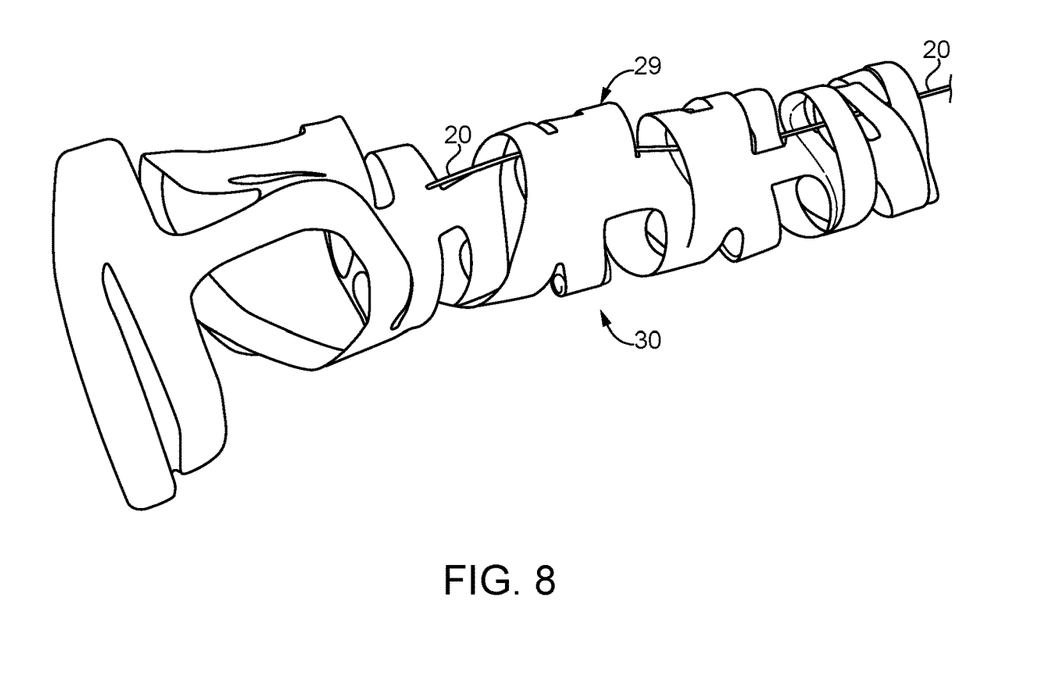
FIG. 8 is a perspective diagrammatic view of the stent of FIG. 1 resiliently unfolding as the trigger wire is withdrawn.
Figure 9:
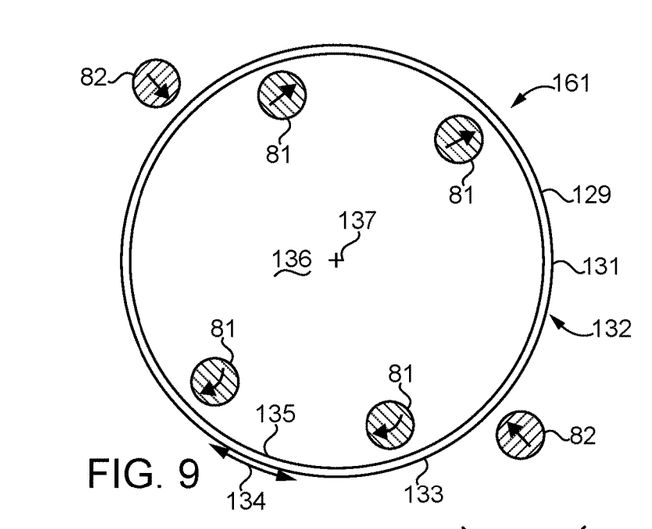
FIG. 9 is a schematic end view of a stent folding procedure according to another aspect of the present disclosure.

After trigger wire 20 has been received in the loops 47, the folding rod 80 may be removed by being slid parallel to longitudinal axis 37 to reveal a cross section 41 as shown in FIG. 6 that is held in the constrained configuration 61 with the trigger wire 20. FIG. 7 shows an end view that is the equivalent of what is shown in FIG. 6. FIG. 8 shows the stent 29 resiliently unfolding toward its tubular rest shape 32 as the trigger wire 20 is withdrawn from one end of framework 31. When the trigger wire 20 is completely withdrawn, the stent assembly 30 will have an unconstrained configuration 60 characterized by the framework 31 resiliently unfolding toward the tubular rest shape 32 as shown in FIG. 1 with the trigger wire 20 out of contact with the framework 31. Preferably, the framework is sufficiently elastic that it can be folded into the folded shape 40 without undergoing plastic deformation. However, some plastic deformation could occur without departing from the present disclosure.

Figure 5:
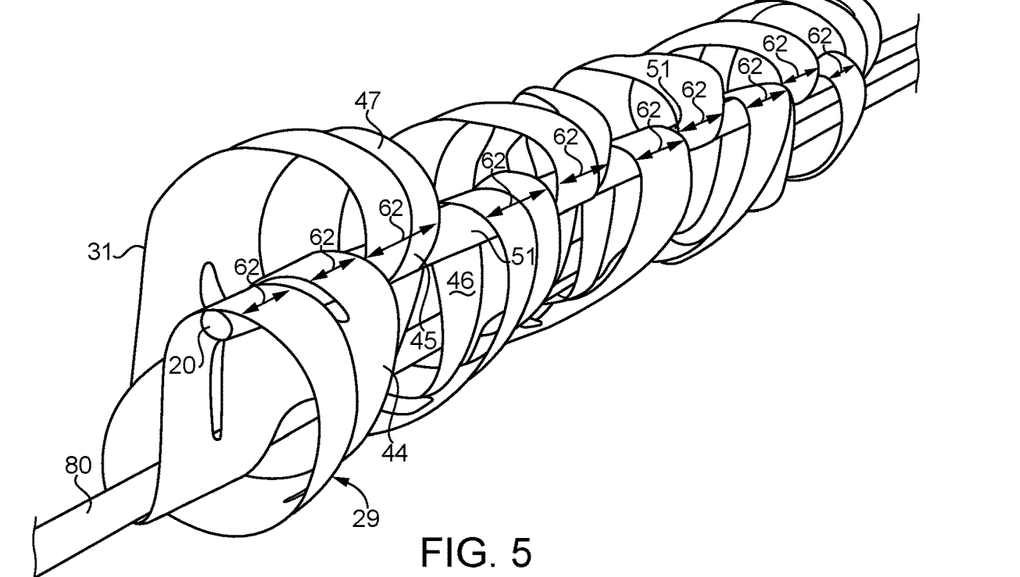
FIG. 5 is a perspective diagrammatic view of the stent of FIG. 1 in a constrained configuration with a trigger wire holding the stent in a folded shape.

The framework 31 pattern, as shown in FIG. 5 is such that each loop 47 is at a matching axial location along longitudinal axis 37 with an associated window 46 so that each respective loop 47 is received in a counterpart respective window 46 to assume the shape shown in FIG. 5. In all cases, it is a constraining segment of the trigger wire 20 that is in contact with the stent 29 and carrying sheer stress to hold the constraining configuration. Each of the windows 46 is cut completely through the wall of the original tube so that the window 46 extends between the internal surface 35 and the external surface 33. The individual loop 47 may be defined by a first portion 45 of the framework 31 to extend through a counterpart window 46 that is defined by a second portion 44 of the framework in the constrained configuration 60 as shown in FIG. 5.

The trigger wire 20 may be manufactured from any suitable material, including but not limited to metallic alloys, plastics or maybe even suture material. A trigger wire 20 according to the present disclosure should have the ability to support the shear stresses that are applied to the trigger wire by the folded framework 31. The trigger wire may have any suitable cross section including but not limited to being round or flat. In the illustrated example of FIGS. 1-7, the trigger wire 20 is a flat rectangular stainless steel wire with a width that is a small fraction of the inner diameter of the framework 31 in the tubular rest shape 32. For instance, the trigger wire may have a width dimension maybe on the order of ⅕ or less of the diameter of the tubular rest shape 32. The width of the trigger wire may be selected based upon a size of the loop 47 when partially flattened. Those skilled in the art will appreciate that the example shown in FIGS. 1-7 show a framework 31 with a pattern that includes exactly one window and exactly one loop in each ring segment 55 location along longitudinal axis 37.

Although this example shows trigger wire 20 being oriented parallel to the longitudinal axis 37 of the stent 29, those skilled in the art will appreciate that non parallel geometries would also fall within the scope of the present disclosure. For instance, those with ordinary skill in the art will appreciate that by changing the framework pattern, the loops 47 and windows 46 could be arranged in a helical pattern without departing from the present disclosure. However, even in those cases, the trigger wire would be oriented more parallel than traverse to the longitudinal axis 37. While it is conceivable that a trigger wire according to the present disclosure could deviate from a parallel relationship with regard to longitudinal axis 37, in no case does a trigger wire according to the present disclosure wrap around the folded framework and contact itself. Thus, wire 320 in U.S. Patent Publication 2002/0045930 could not be considered to be a trigger wire according to the present disclosure. Because the windows 46 are larger than the counterpart loops 47 to be received therein, the constraining segments 51 of the trigger wire are in contact with discrete locations of the internal surface 35 at a plurality of locations along the length 63 of stent 29. When the trigger wire 20 is withdrawn from the constrained configuration 61 as shown in FIG. 8, the framework 31 resiliently unfolds toward the tubular rest shape 32.

Figure 10:
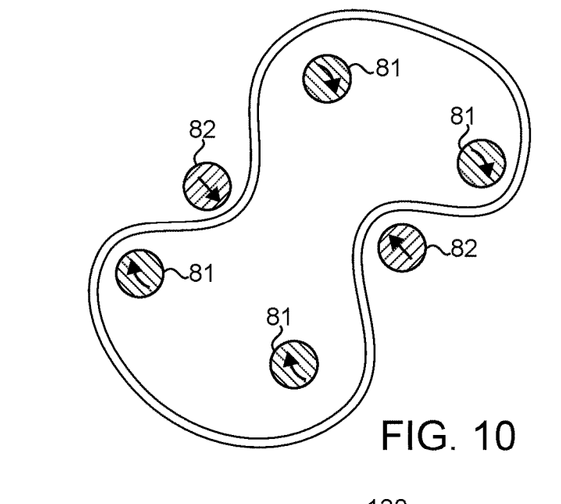
FIG. 10 is a further step in the folding procedure for the stent of FIG. 9.
Figure 11:
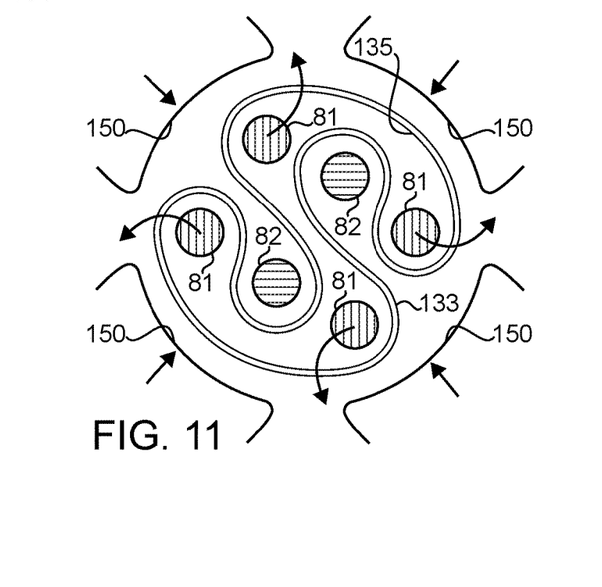
FIG. 11 is a further progression in the folding of the stent of FIGS. 9 and 10.
Figure 12:
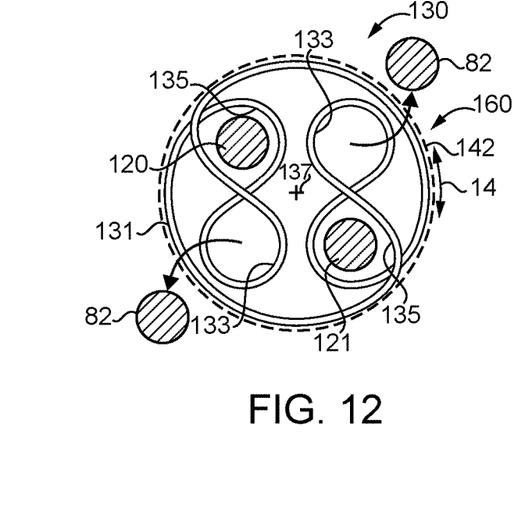
FIG. 12 is an end view of the stent of FIG. 9 held in a folded configuration by two trigger wires.

Referring now to FIGS. 9-12, a stent assembly according to another embodiment has at least two sets of loops and windows in each ring segment longitudinal location along longitudinal axis 137 so that the folded stent 129 is held in its constrained configuration 161 by two trigger wires 120 and 121, versus a single trigger wire 20 as in the previous embodiment. With this greater complexity, a more complex effort may be necessary to change the framework 131 from the tubular rest shape 132 shown in FIG. 9 to a folded shape 140 that is held in the constrained configuration 160 by two trigger wires 120 and 121. In this example, the folding process may begin by first positioning four internal folding rods 81 within the passageway 136 defined by the internal surface 135 of framework 131. Two external folding rods 82 contact the external surface 133 and press inward in parallel directions as shown in FIG. 10 to eventually arrive at the partially folded configuration shown in FIG. 11. At this point, the four internal folding rods 81 may be removed provided that some external constraint is brought to bear upon the exposed external surface 133 in the partially folded configuration. The arrows in FIG. 11 suggest that the folding rods 81 are removed, but they are removed by being slid into or out of the page along longitudinal axis 137. In the illustrated example, four external compression supports 150 are pushed toward a center of the folded cross section to allow removal of the internal folding rods 81 while maintaining the stent 129 in the partially folded configuration. After the internal folding rods 81 have been removed, the windows and loops (not visible) of the framework 131 may now be received in one another to allow trigger wires 120 and 121 to be passed through the aligned loops to hold the stent assembly 130 in the constrained configuration 160 as shown in FIG. 12. When this is done, the previously positioned external folding rods 82 may now be removed, such as by being slid parallel to axis 137. The end result is the framework 131 being held in a folded shape 140 with a cross section 141 perpendicular to the longitudinal axis that fits in a closed shape 142, such as a circle, having a perimeter 143 that is smaller than the expanded perimeter 134 of the framework 131 in the tubular rest shape 132 shown in FIG. 9.

Figure 13:
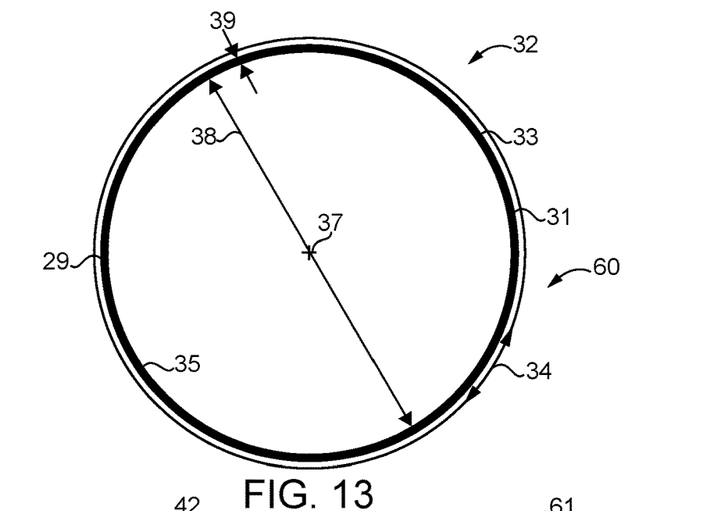
FIG. 13 is a schematic end view of a stent according to another aspect of the present disclosure.
Figure 14:
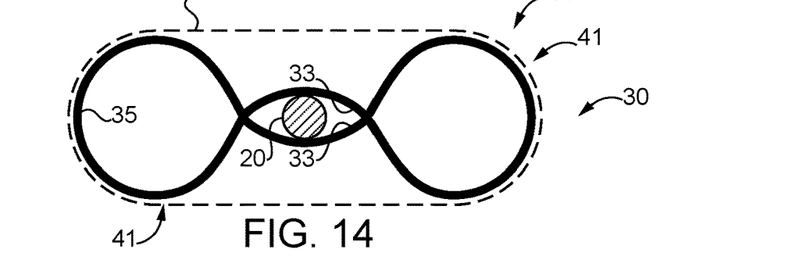
FIG. 14 is an end view of the stent of FIG. 13 held in a constrained folded shape with a trigger wire.

Referring now to FIGS. 13 and 14, an alternative strategy for folding the stent 29 of FIGS. 1-7 is used to illustrate the fact that the cross section 41 and the folding shape 40 may fit in a closed shape 42, which has a race track oval shape, having a perimeter 43 that is still less than the expanded perimeter 34 of the framework 31 in the tubular rest shape 32 as shown in FIG. 13. This alternative folding strategy is held in the constrained configuration 61 with the trigger wire in contact with an external surface of framework 31 rather than an internal surface as shown in the folded strategy of FIGS. 1-7. Depending upon the structure of the framework 31 in the area of the loops that are on either side of trigger wire 20, the framework 31 may be capable of being further folded to interlace those left and right loops to be held with a second trigger wire. In such a case the additional trigger wire would be in contact with the internal surface 35 of framework 31, while at the same time being partially constrained by the original trigger wire 20 shown as in contact with the outer surface 33 of framework 31. In all cases illustrated in the present disclosure, each trigger wire is in contact exclusively with one, but not both, of the internal surface and the external surface in order to hold, or partially hold, the folded stent in a constrained configuration. Thus those skilled in the art will appreciate that, depending upon the framework pattern, one, two or maybe even more trigger wires may be used to hold the stent in its folded configuration. Those skilled in the art will appreciate that different framework patterns enable different options as far as the size of the cross section in the folded shape, and what number of trigger wires are needed to hold it in the folded shape, and in what surfaces (internal or external) that the respective trigger wire(s) is in contact with in order to hold the stent in the constrained configuration. In most instances, the closed shape within which the cross section of the folded shape will fit will often preferably be a circle as in the embodiments of FIGS. 1-7 and 9-12 but could be an alternative shape, such as the oblong race track closed shape 42 shown in FIG. 14. In all cases, the perimeter of the closed shape is measurable by starting at a given point on the boundary and measuring along that boundary until one returns to the starting point.

It has been found that thin walled shaped memory tubes may work best as a framework according to the present disclosure. In most instances, the tubular rest shape 31 will have a diameter 38 that is between one and two orders of magnitude greater than a wall thickness 39 of framework 31. Nevertheless, dimensions outside of this range could also fall within the intended scope of the present disclosure.

Figure 15:
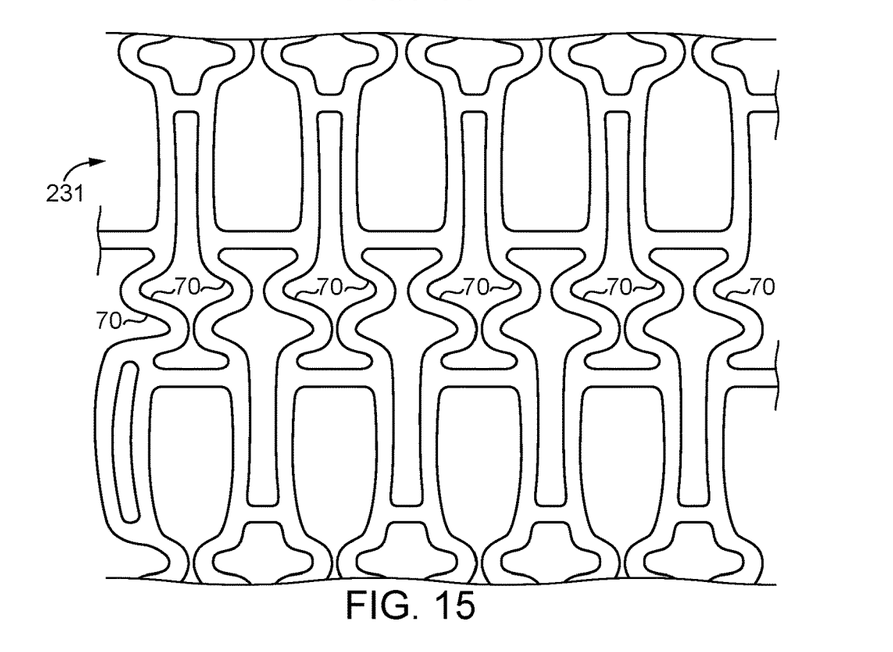
FIG. 15 is a flat layout cut pattern for a stent according to another aspect of the present disclosure that includes radial compliance segments.

Referring now in addition to FIG. 15, an alternative framework pattern 231 is illustrated that includes a plurality of radial compliance segments 70 that allow the stent in its tubular rest shape to respond to radial forces by either decreasing or increasing in diameter due to deformations of the radial compliance segments 70 that are distributed along the length of framework 231. For instance, this strategy might be utilized if the stent 231 would be implanted in a vessel with a slightly smaller internal diameter than the diameter of the framework in its tubular rest shape. In those circumstances, as the stent unfolded, the radial forces applied to the stent by the vessel wall could result in a slight deformation of the radial compliance segments 70 so that the stent has a slightly smaller diameter than its tubular rest shape in order to match the internal diameter of the vessel in which it is implanted. Alternatively, the radial compliance segments might be deformed, such as by using a balloon catheter within the stent after unfolding in order to increase its diameter at an implantation site. Those skilled in the art will appreciate that the radial compliance segments 70 may facilitate pulsatile flexing in a vessel and/or the use of a balloon catheter post dilation for anchoring and to accommodate sizing errors.

Figure 16:
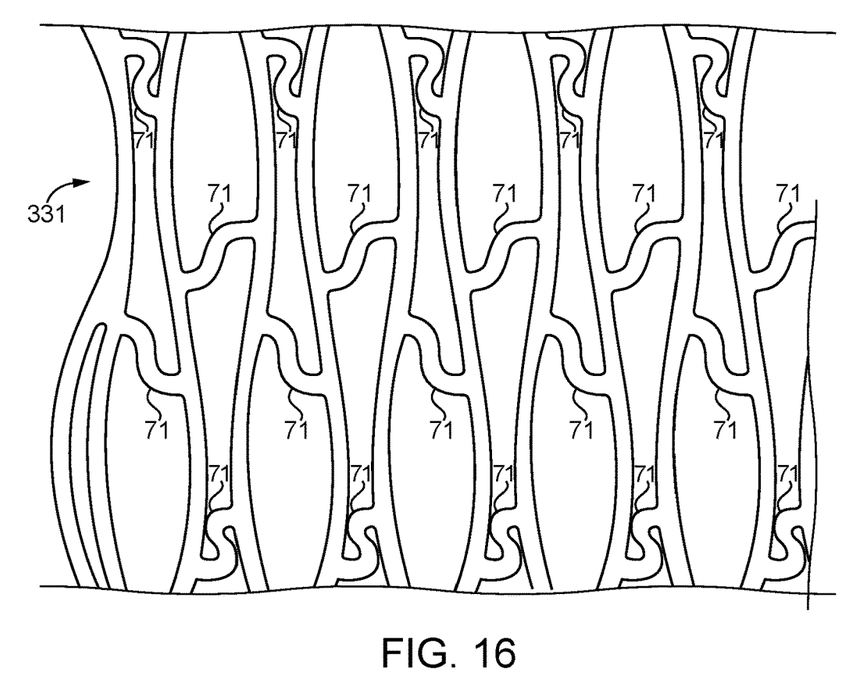
FIG. 16 is a flat layout cut pattern for a cannula cut stent according to still another embodiment of the present disclosure that includes longitudinal compliance segments.

Referring now to FIG. 16, a framework pattern 331 according to another embodiment of the present disclosure includes a plurality of longitudinal compliance segments 71 distributed along the length of the framework to allow the framework 331 to stretch or compress along different longitudinal segments of the framework 331. For instance, this strategy may permit the stent to unfold and then easily comply with a curved passageway, for instance, slightly compressing longitudinal compliance segment 71 on one side of the stent while lengthening the counterpart longitudinal compliance segments 71 on the opposite side of the stent. Those skilled in the art will appreciate that other framework patterns could also include both radial compliance segments and longitudinal compliance segments distributed around the expanded perimeter of the framework without departing from the present disclosure. Longitudinal compliance segments may facilitate matching the curvature of a vessel being stented and/or better tolerate flexing of vessels and limbs such as those around joints after the stent is implanted.

Figure 17:
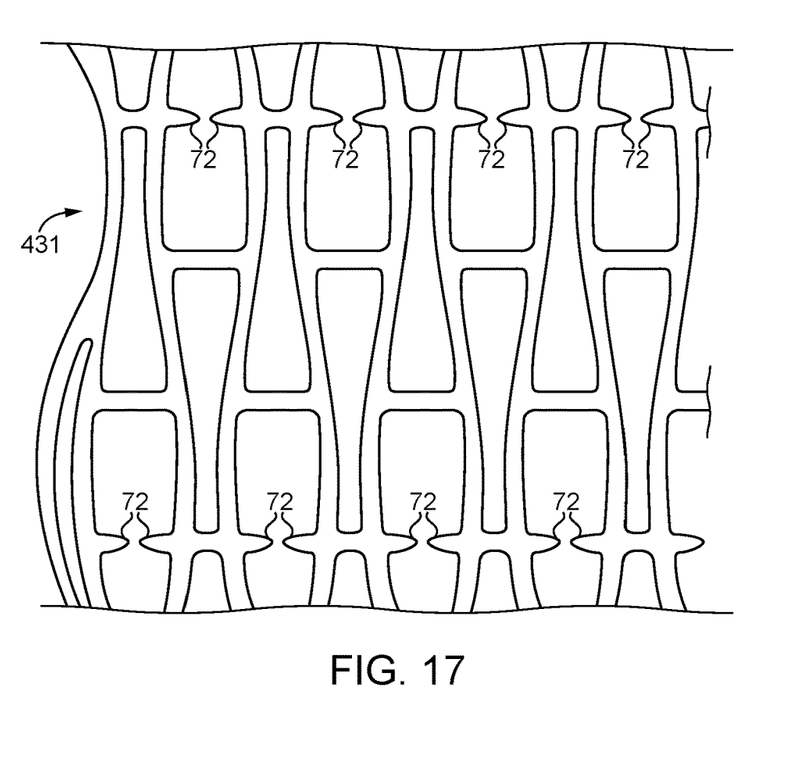
FIG. 17 is a flat layout cut pattern for a stent according to the present disclosure that includes barbs.

Referring now to FIG. 17, framework pattern 431 according to still another embodiment of the present disclosure may include a plurality of barbs 72 distributed at locations around the expanded perimeter. These barbs 72 may be deformed during manufacture so that they extend radially away from the expanded perimeter when the framework 431 is in its tubular rest shape so that the barbs 72 may engage a vessel wall to assist in keeping the stent in a location without risk of migration. Due to the longitudinal folding strategy of the present disclosure, the barbs 72 can be positioned with respect to the windows 46 and loops 47 to be nested in folds of the framework when the framework 231 is in its folded shape. Those skilled in the art will appreciate that foldable framework patterns having any combination of barbs, longitudinal compliance segments, radial compliance segments or none of these would all fall within the intended scope of the present disclosure. The anchoring barbs 72 may be plastically deformed during manufacturing to bring them out of plane with the outer surface of the stent. These anchoring barbs 72 may then be nested in folds of the stent when it is in its folded constrained configuration during introduction, but the barbs are exposed for maximum functionality once the stent has been deployed to an unfolded diameter. The anchoring barbs 72 could facilitate purchase in the walls or vessels being brought together for the purpose of anastomosis as well.

INDUSTRIAL APPLICABILITY

The present disclosure finds potential application in any stenting procedure. Although the illustrated embodiments show uncovered stents, the present disclosure could also apply to any place a stent graft is intended to be utilized. Thus, the present disclosure could also apply to covered stents. In addition, the present disclosure could find potential application in facilitating end-to-end anastomosis. The present disclosure finds particular application in any situation where the stent must be held in a small low profile cross section for being maneuvered to an implantation site, and then have the ability to resiliently self un-fold into a tubular rest shape at the site.

Figure 18:
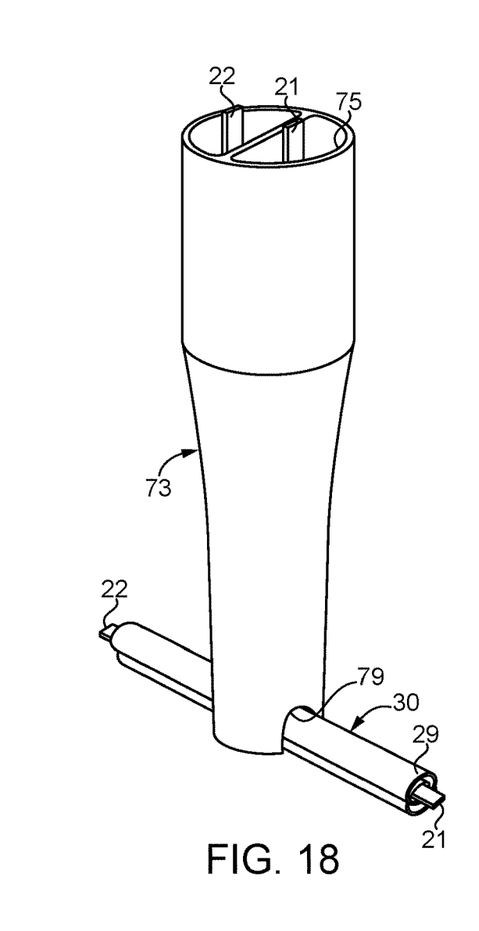
FIG. 18 is a perspective view of an end-to-end anastomosis tool assembly that includes a folded constrained stent according to the present disclosure.
Figure 19:
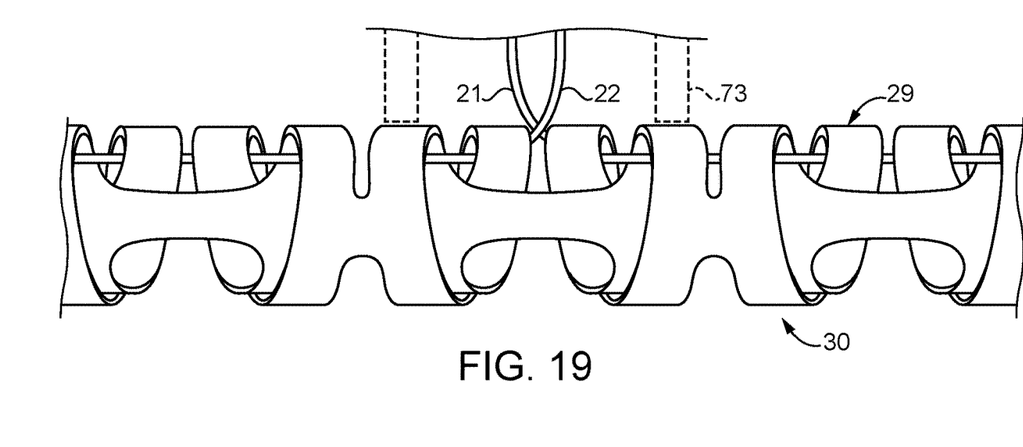
FIG. 19 is a perspective view of the folded constrained stent of FIG. 18 with the handle omitted.
Figure 20:
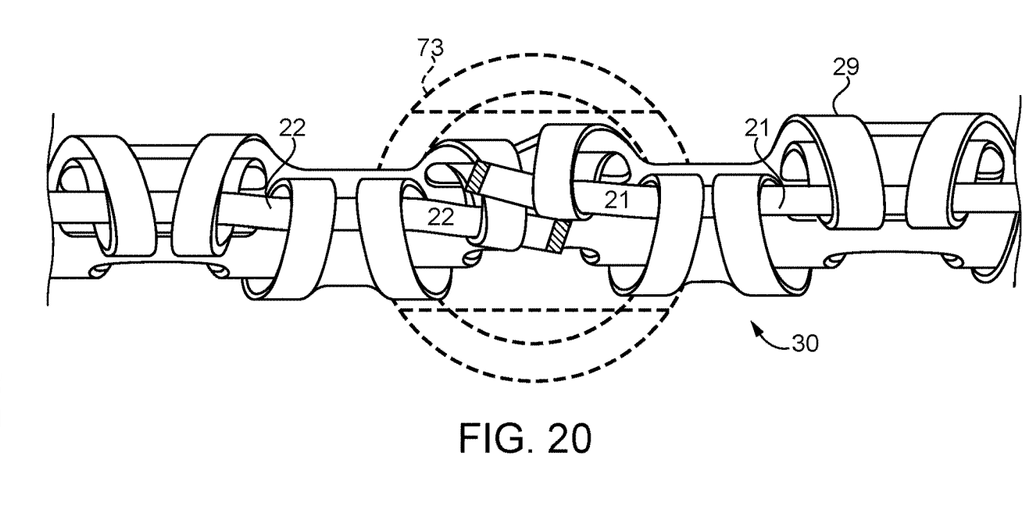
FIG. 20 is another perspective view of the stent of FIGS. 18 and 19 as viewed along the barrel of the omitted handle.
Figure 21:
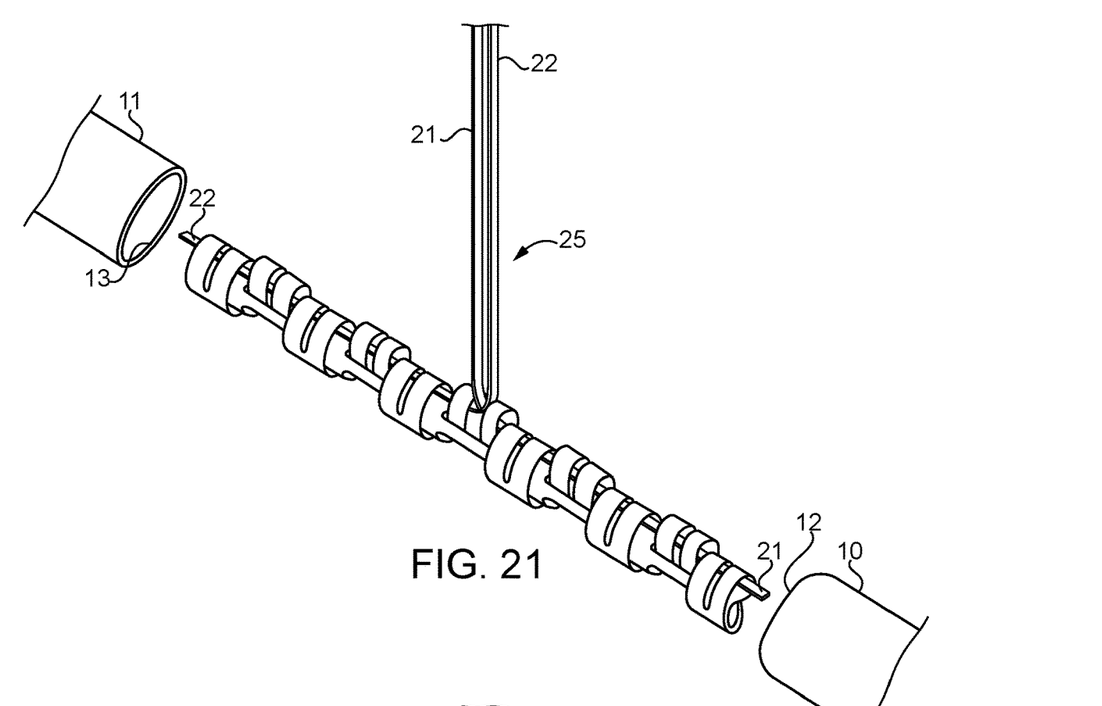
FIG. 21 is a perspective view of a step in a procedure of forming an end-to-end anastomosis with a stent according to the present disclosure.
Figure 22:
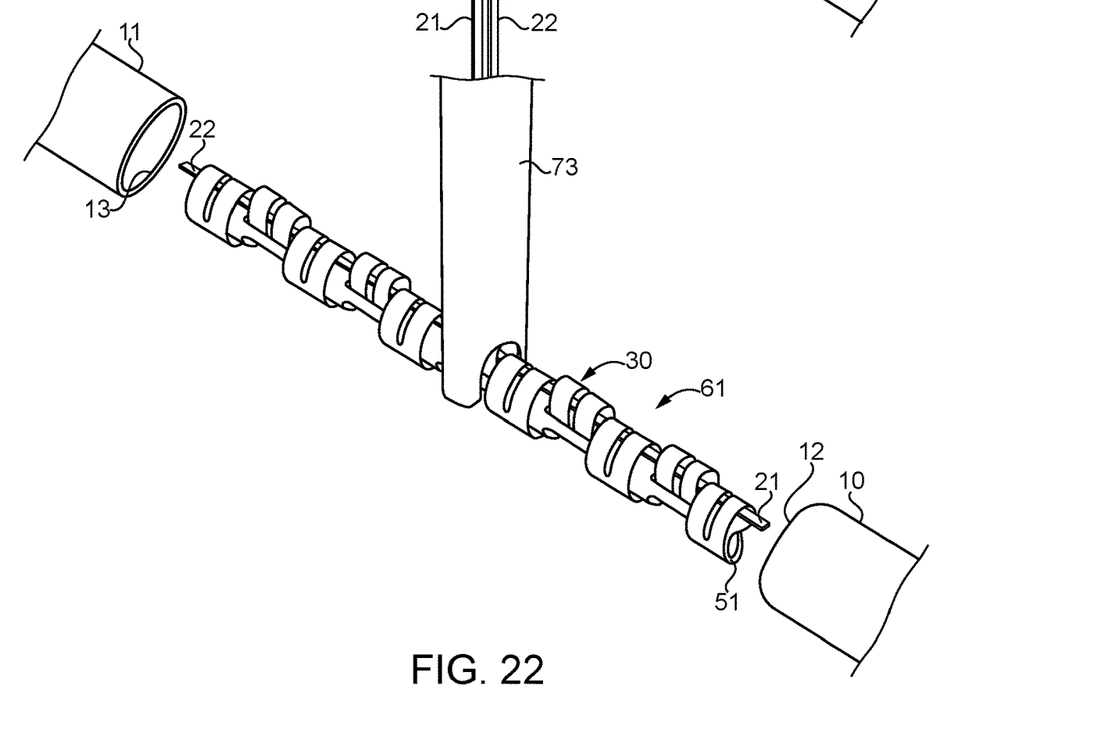
FIG. 22 is a view similar to FIG. 21 except showing the handle portion engaging the stent prior to insertion in the vessels.

Referring now to FIGS. 18-27, a series of images show how a stent assembly 30 according to the present disclosure can be used to form an end-to-end anastomosis. In particular, this illustration utilizes a stent 29 having a framework 31 as per FIGS. 1-7, but includes two trigger wires that each emerge from a middle portion 49 of the stent in its folded configuration and travel up through a hollow handle 73 for manipulation by a user. In particular, handle 73 may include a pair of cut outs 74 that allow the handle to straddle stent assembly 30. Those skilled in the art will appreciate that handles having a wide variety of shapes for mating with the folded stent assembly 30 would all fall within the intended scope of the present disclosure. As best shown in FIGS. 19 and 20, the two trigger wires 21 and 22 are associated with the left and right halves, respectively, of the folded stent assembly. The trigger wires 21 and 22 emerge from the folded stent at a middle portion 49 of framework 31 and travel up through the center of the handle 73 and emerge on its remote end for grasping by a user. The frictional interaction between the trigger wires 21 and 22 and the folded framework 31 may be sufficient to hold the handle 73 in place as the assembly as shown in FIG. 18. FIG. 21 shows the manipulation assembly, with handle 73 omitted, but with the stent assembly 30 positioned between a first vessel 10 and a second vessel 11 to be joined in an anastomosis according to the present disclosure. FIG. 22 is identical to FIG. 21 except including handle 73.

Figure 23:
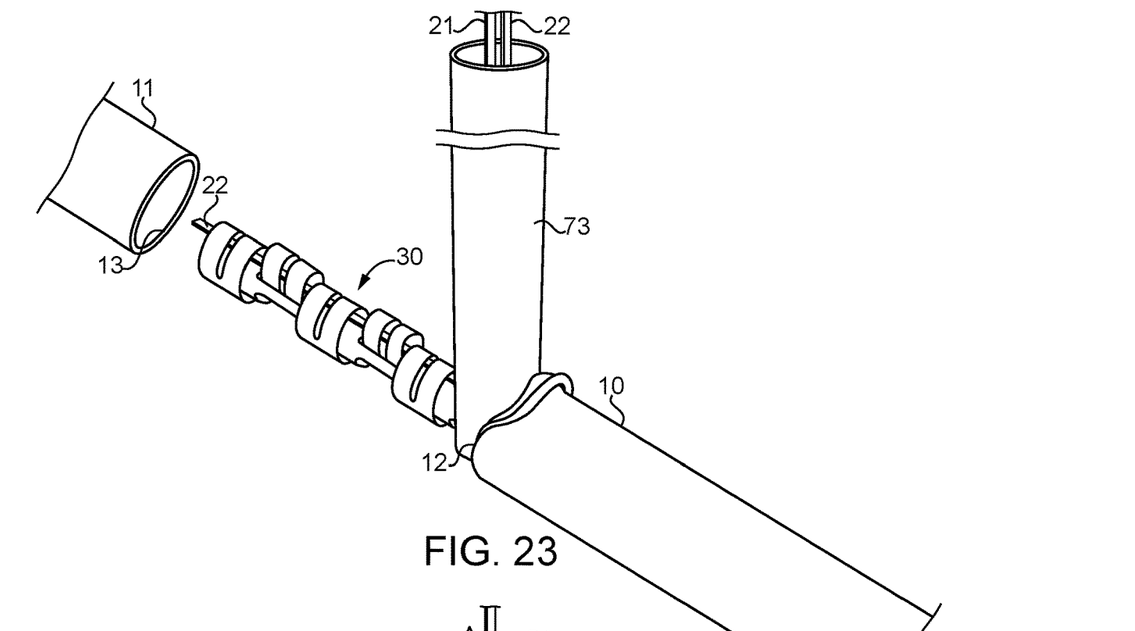
FIG. 23 shows the one half of the folded constrained stent received in a first vessel.
Figure 24:
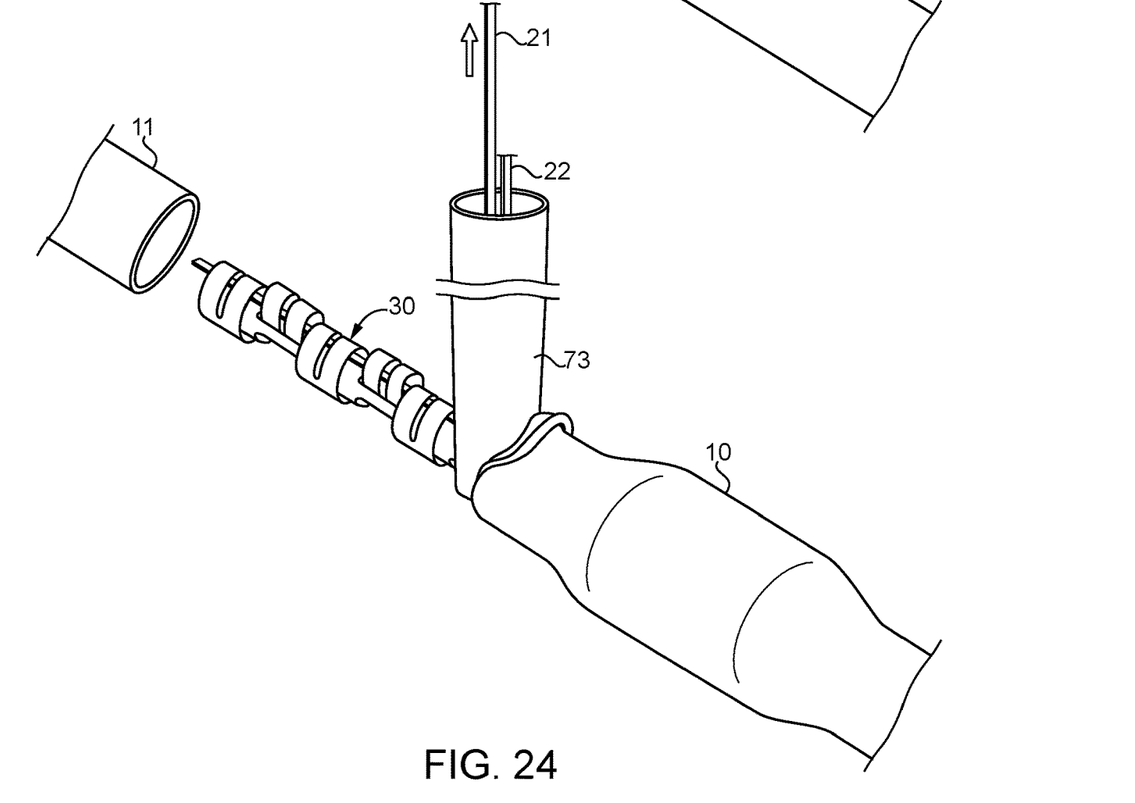
FIG. 24 shows the procedure with the portion of the stent positioned in the vessel partially expanded.
Figures 25, 26:
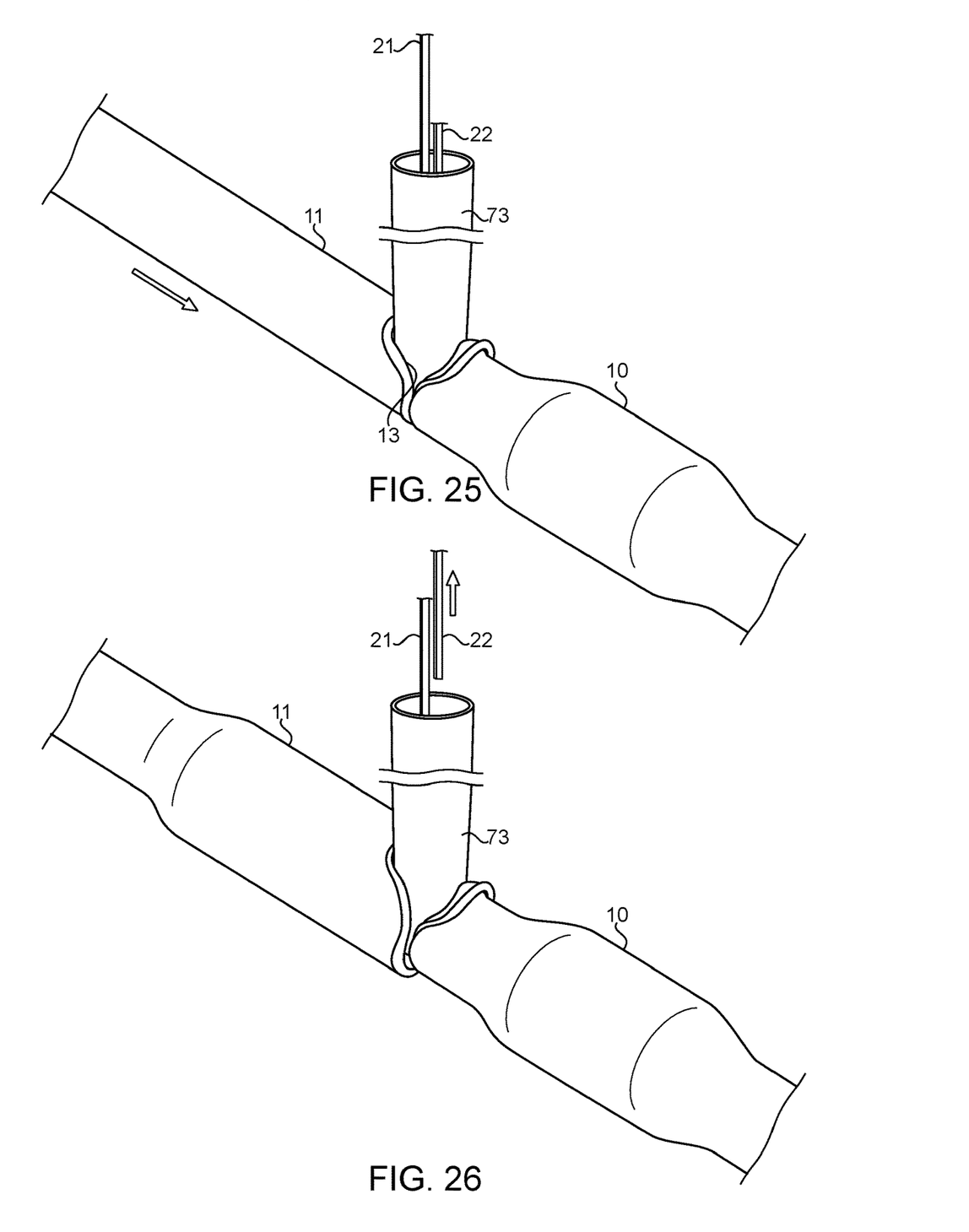
FIG. 25 is a perspective view showing the second half of the stent received in the second vessel.
FIG. 26 is a perspective view showing the stent expanded in the second vessel.
Figures 27, 28:
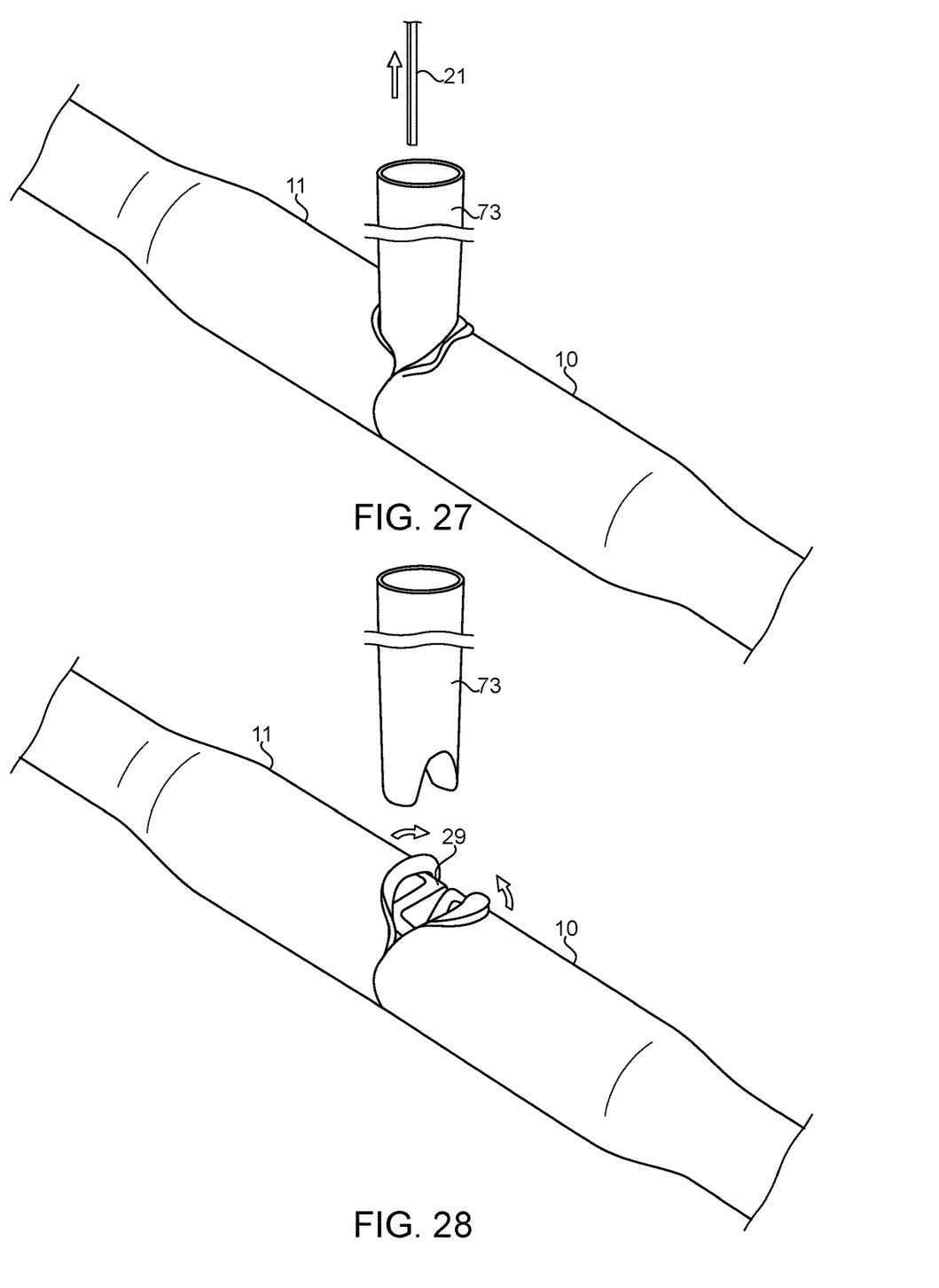
FIG. 27 shows a further step in the procedure in which the stent has been completely expanded in the two vessels to be joined.
FIG. 28 shows a later step in the procedure with the handle being moved away from the now expanded stent joining the two vessels.

In a first step of joining the two vessels end-to-end, one end 51 of stent assembly 30 is slid into the open end 12 first vessel 10, preferably to the point where the end of the vessel contacts handle 73. As shown in FIG. 23. Next, the first trigger wire 21 is pulled a distance sufficient to partially expand the end of the stent assembly 13 positioned in first vessel 10 as shown in FIG. 24. By partially expanding stent 29 in the first vessel 10, the risk of the stent slipping back out before the procedure is completed is reduced. Next, as shown in FIG. 25, the opposite end of the stent assembly 30 is slid, while in a constrained configuration, into the open end 13 of the second vessel 11. Next, as shown in FIG. 26, the second trigger wire 22 is completely withdrawn to fully expand the half of the stent in the second vessel 11 as shown in FIG. 26. Thereafter, the first trigger wire 21 is completely withdrawn to fully expand the stent in both vessels 10, 11. When this is done, the stent assembly 30 is changed from the constrained configuration to an unconstrained configuration (tubular rest shape) responsive to moving the at least one trigger wire from being in contact with the framework of the stent assembly to a position out of contact with the framework 31. The framework responds by resiliently unfolding from the folded shape toward the tubular rest shape after the second trigger wire 22 is withdrawn, and the handle 73 may be moved away as shown in FIG. 28. Thereafter, the exposed ends of the vessels 10 and 11 may be finally secured with an adhesive or some other suitable strategy (e.g. suture(s)) to prevent leakage after blood flow is resumed in the now joined vessels 10-11.

Those skilled in the art will appreciate that the first and second trigger wires 21 and 22 each includes segments 25 that extend perpendicularly away from the longitudinal axis 37 of the stent assembly 30 in its constrained configuration 60 as best shown in FIG. 21. Prior to removal of the handle 73, the handle may remain in contact with the middle portion 49 of the framework 31 during the step of sliding the assembly into the vessels and changing from the folded shape to the tubular rest shape. When actually expanding the stent in the vessels 10 and 11, the respective trigger wire is moved through the hollow interior 75 of the handle 73. During the sliding steps shown in FIGS. 23 and 25, the framework 31 may be considered to be connected to the handle 73 by the first and second trigger wires 21 and 22.

The present description is for illustrative purposes only, and should not be construed to narrow the breadth of the present disclosure in any way. Thus, those skilled in the art will appreciate that various modifications might be made to the presently disclosed embodiments without departing from the full and fair scope and spirit of the present disclosure.

Other aspects, features and advantages will be apparent upon an examination of the attached drawings and appended claims.

What is claimed is:

1. A stent assembly comprising:
a framework having a tubular rest shape that defines a longitudinal axis, has an external surface that defines an expanded perimeter, a length along the longitudinal axis, and an internal surface that defines a passageway;
a trigger wire;
the framework having a folded shape in which the framework is folded in on itself into a cross section perpendicular to the longitudinal axis at each location along the length that fits within a closed shape having a perimeter that is smaller than the expanded perimeter;
wherein the stent assembly has a constrained configuration characterized by the framework being held in the folded shape by the trigger wire being in contact with at least one of the internal surface and the external surface to apply a shear force to the trigger wire perpendicular to the longitudinal axis responsive to a bias of the framework to resiliently unfold; and
wherein the stent assembly has an unconstrained configuration characterized by the framework being in the tubular rest shape with the trigger wire out of contact with the framework.

2. The stent assembly of claim 1 wherein the framework defines a window that extends between the internal surface and the external surface.

3. The stent assembly of claim 2 wherein a first portion of the framework extends through the window, which is defined by a second portion of the framework, in the constrained configuration.

4. The stent assembly of claim 3 wherein the first portion defines a loop that extends through the window in the folded shape; and
the trigger wire extends through the loop in the constrained configuration.

5. The stent assembly of claim 4 wherein the framework defines a plurality of windows and a plurality of loops;
each of the loops is received in a respective one of the plurality of windows; and
the trigger wire extends through the loops in the constrained configuration.

6. The stent assembly of claim 1 wherein the trigger wire includes a constraining segment that is in contact with the internal surface and oriented more parallel than transverse to the longitudinal axis.

7. The stent assembly of claim 6 wherein the constraining segment of the trigger wire extends parallel to the longitudinal axis.

8. The stent assembly of claim 1 wherein the tubular rest shape has a diameter that is between one and two orders of magnitude greater than a wall thickness of the framework.

9. The stent assembly claim 1 wherein the framework includes a plurality of radial compliance segments distributed around the expanded perimeter.

10. The stent assembly of claim 1 wherein the framework includes a plurality of longitudinal compliance segments distributed around the expanded perimeter.

11. A stent assembly comprising:
a framework having a tubular rest shape that defines a longitudinal axis, has an external surface that defines an expanded perimeter; and an internal surface that defines a passageway;
a trigger wire;
the framework having a folded shape in which the framework is folded in on itself into a cross section perpendicular to the longitudinal axis that fits within a closed shape having a perimeter that is smaller than the expanded perimeter;
wherein the stent assembly has a constrained configuration characterized by the framework being held in the folded shape by the trigger wire being in contact with at least one of the internal surface and the external surface to apply a shear force to the trigger wire perpendicular to the longitudinal axis responsive to a bias of the framework to resiliently unfold;
wherein the stent assembly has an unconstrained configuration characterized by the framework being in the tubular rest shape with the trigger wire out of contact with the framework;
wherein the trigger wire includes a constraining segment that is in contact with the internal surface and oriented more parallel than transverse to the longitudinal axis;
wherein the constraining segment of the trigger wire extends parallel to the longitudinal axis; and
wherein the trigger wire is one of two trigger wires that are oriented parallel to each other.

12. The stent assembly of claim 11 wherein the constraining segment of one of the two trigger wires extends in an opposite direction to a constraining segment of an other one of the two trigger wires.

13. A stent assembly comprising:
a framework having a tubular rest shape that defines a longitudinal axis, has an external surface that defines an expanded perimeter, and an internal surface that defines a passageway;
a trigger wire;
the framework having a folded shape in which the framework is folded in on itself into a cross section perpendicular to the longitudinal axis that fits within a closed shape having a perimeter that is smaller than the expanded perimeter;
wherein the stent assembly has a constrained configuration characterized by the framework being held in the folded shape by the trigger wire being in contact with at least one of the internal surface and the external surface to apply a shear force to the trigger wire perpendicular to the longitudinal axis responsive to a bias of the framework to resiliently unfold;
wherein the stent assembly has an unconstrained configuration characterized by the framework being in the tubular rest shape with the trigger wire out of contact with the framework;
wherein the framework includes a plurality of barbs that extend radially away from the expanded perimeter when the framework is in the tubular rest shape; and
the barbs are nested in folds of the framework when the framework is in the folded shape.

* * * * *